United States Patent
Richards et al.

(10) Patent No.: US 10,588,837 B2
(45) Date of Patent: Mar. 17, 2020

(54) OXIDATIVE COLORATION OF HAIR WITH REDUCED HAIR DAMAGE

(71) Applicant: Conopco, Inc., Englewood Cliffs, NJ (US)

(72) Inventors: Claire Louise Richards, Wrexham (GB); Anne-Sophie Piggott, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/079,646

(22) PCT Filed: Jan. 26, 2017

(86) PCT No.: PCT/EP2017/051666
§ 371 (c)(1),
(2) Date: Aug. 24, 2018

(87) PCT Pub. No.: WO2017/148629
PCT Pub. Date: Sep. 8, 2017

(65) Prior Publication Data
US 2019/0070082 A1    Mar. 7, 2019

(30) Foreign Application Priority Data

Feb. 29, 2016    (EP) ................................... 16157870

(51) Int. Cl.
*A61Q 5/10*    (2006.01)
*A61K 8/36*    (2006.01)

(52) U.S. Cl.
CPC ................ *A61K 8/361* (2013.01); *A61Q 5/10* (2013.01); *A61K 2800/43* (2013.01); *A61K 2800/5922* (2013.01); *A61K 2800/882* (2013.01)

(58) Field of Classification Search
CPC ........ A61Q 5/10; A61K 8/411; A61K 8/4926; A61K 8/415; A61K 8/22; A61K 8/4324; A61K 8/361; A61K 8/92; A61K 47/44
See application file for complete search history.

(56) References Cited

U.S. PATENT DOCUMENTS

| | | |
|---|---|---|
| 4,357,141 A | 11/1982 | Grollier et al. |
| 2009/0070945 A1 | 3/2009 | Nguyen et al. |
| 2012/0317734 A1 | 12/2012 | Martinez-Santiago et al. |

FOREIGN PATENT DOCUMENTS

| | | | |
|---|---|---|---|
| CN | 101756815 | 8/2012 | |
| CN | 103271844 A | * 4/2013 | ............... A61Q 5/10 |
| CN | 103271844 | 9/2013 | |
| EP | 0223572 | 5/1987 | |
| EP | 100913730 | 8/2009 | |
| EP | 2308564 | 4/2011 | |
| GB | 2476431 | 6/2011 | |
| KR | 20140043548 | 4/2014 | |
| WO | WO2012175688 | 12/2012 | |
| WO | WO2012175690 | 12/2012 | |

OTHER PUBLICATIONS

English Abstract of the Patent No. KR 2014/043548 (Apr. 10, 2014).*
Search Report and Written Opinion in PCTEP2017051666; dated Mar. 10, 2017.
Search Report and Written Opinion in EP16157870; dated Jun. 8, 2016.

* cited by examiner

*Primary Examiner* — Eisa B Elhilo
(74) *Attorney, Agent, or Firm* — Foley & Lardner LLP

(57) ABSTRACT

The invention provides a packaged composition for the oxidative coloration of hair which is formulated in two parts, the composition comprising: (i) an aqueous hair colorant part comprising one or more oxidative dye precursors, and less than 1% oleic acid by weight based on total weight of part (i); (ii) an aqueous colour developer part comprising one or more oxidising agents, at least 5% stearic acid by weight based on total weight of part (ii); and less than 1% oleic acid by weight based on total weight of part (ii); in which parts (i) and (ii) are adapted to be mixed together before application to the hair. The compositions provide an improved level of hair damage protection during the colouring process without compromising on colour delivery.

7 Claims, No Drawings

OXIDATIVE COLORATION OF HAIR WITH REDUCED HAIR DAMAGE

The present invention relates to compositions and methods for reducing hair damage during oxidative coloration.

BACKGROUND OF THE INVENTION

There are generally three types of hair colouring system in widespread use: permanent, semi-permanent, or temporary. The term "permanent hair colorant" generally refers to oxidative hair colouring agents in which oxidative dye precursors diffuse into the hair through the cuticle and into the cortex, where they can then undergo oxidative coupling reactions in the presence of suitable oxidizing agents to form the end dye molecules which produce colour inside the hair.

Permanent hair colorants are very popular with consumers since they provide vibrant and multi-dimensional colour which is relatively unaffected by light, shampooing and perspiration. However the process is not without drawbacks. Repeated oxidative treatments over prolonged periods may damage or weaken hair, making it prone to breakage and reduced lustre. In an effort to address this problem, many permanent hair colorants are sold with a conditioner. The application of a conditioner deposits a protective layer of conditioning agent onto the hair and results in an improved feel, but it does not protect against damage as such, since it is applied on hair after the colorant has been rinsed off.

Accordingly, there remains a need for oxidative hair colouring compositions which can provide an improved level of hair damage protection during the colouring process. In particular there remains a need for oxidative hair colouring compositions which can provide this improved protection without compromising on colour delivery.

The present invention addresses this problem.

SUMMARY OF THE INVENTION

The present invention provides a packaged composition for the oxidative coloration of hair which is formulated in two parts, the composition comprising:

(i) an aqueous hair colorant part comprising one or more oxidative dye precursors, and less than 1% oleic acid by weight based on total weight of part (i);

(ii) an aqueous colour developer part comprising one or more oxidising agents, at least 5% stearic acid by weight based on total weight of part (ii); and less than 1% oleic acid by weight based on total weight of part (ii);

in which parts (i) and (ii) are adapted to be mixed together before application to the hair.

DESCRIPTION OF THE INVENTION

The hair colorant part (i) comprises one or more oxidative dye precursors. The term "oxidative dye precursor" in the context of this invention means materials which are operable, when combined with an aqueous oxidizing agent, to impart colour to the hair. Generally such oxidative dye precursors include primary intermediates and optionally couplers for the formation of oxidative dyes. Primary intermediates yield colour on oxidation. Couplers do not form dyes on oxidation but do produce colour changes when used with primary intermediates.

Primary intermediates mainly belong to three classes of aromatic compounds: diamines, aminophenols and phenols. Examples include ortho- or para-substituted aminophenols or phenylenediamines and cosmetically acceptable salts thereof.

Suitable primary intermediates for use in part (i) include:
p-phenylenediamines such as: benzene-1,4-diamine (commonly known as p-phenylenediamine or PPD), 2-methyl-benzene-1,4-diamine (commonly known as p-toluenediamine or PTD); 2-[(4-aminophenyl)-(2-hydroxyethyl)-amino]-ethanol, (commonly known as N,N-bis(2-hydroxyethyl)-p-phenylenediamine); 2-chloro-p-phenylenediamine; N-phenyl-p-phenylenediamine; N-2-methoxyethyl-p-phenylenediamine; N,N-bis-(2-hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-bis-(N-hydroxyethyl)-N-(4-aminophenyl)amino)-2-propanol; 2-methyl-4-dimethylaminoaniline; and cosmetically acceptable salts thereof and combinations thereof. Preferred p-phenylenediamines include: p-toluenediamine; p-phenylenediamine; N-2-methoxyethyl-p-phenylenediamine; N,N-bis-(2-hydroxyethyl)-p-phenylenediamine; 2-hydroxyethyl-p-phenylenediamine; and cosmetically acceptable salts thereof and combinations thereof.

p-aminophenols such as: 4-aminophenol (commonly known as p-aminophenol); p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; 5-aminosalicylic acid; and cosmetically acceptable salts thereof and combinations thereof.

Preferred p-aminophenol derivatives include: p-aminophenol; p-methylaminophenol; 3-methyl-p-aminophenol; 2-methyl-p-aminophenol; 2-(2'-hydroxyethylaminomethyl)-p-aminophenol; 2-methoxymethyl-p-aminophenol; 5-aminosalicylic acid; and cosmetically acceptable salts thereof and combinations thereof.

o-phenylenediamines such as: 3,4-diaminobenzoic acid and cosmetically acceptable salts thereof.

o-aminophenols such as: 2-aminophenol (commonly known as o-aminophenol); 2,4-diaminophenol; 2-amino-5-methyl-phenol; 2-amino-6-methyl-phenol; N-(4-amino-3-hydroxy-phenyl)-acetamide; 2-amino-4-methyl-phenol; and cosmetically acceptable salts thereof and combinations thereof.

heterocyclics such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; 2-N,2-N-dimethyl-pyridine-2,5-diamine; 1-(4-aminophenyl)-2-pyrrolidinemethanol; N-(4-aminophenyl)-4-hydroxy-2-pyrrolidinemethanol; 4-hydroxy-2,5,6-triaminopyrimidine; 1-(2'hydroxyethyl)-amino-3,4-methylene dioxybenzene; 1-hydroxyethyl-4,5-diaminopyrazole; and cosmetically acceptable salts thereof and combinations thereof.

Particularly preferred primary intermediates include: p-phenylenediamine; p-toluenediamine; p-aminophenol; 3-methyl-p-aminophenol; N,N-bis(2-hydroxyethyl)-p-phenylenediamine; 2-hydroxyethyl-p-phenylenediamine; 1-hydroxyethyl-4,5-diaminopyrazole; and cosmetically acceptable salts thereof and combinations thereof.

Mixtures of any of the above-described materials may also be used.

Primary intermediates are generally used in approximately equimolar quantities with respect to couplers, for example at a molar ratio of primary intermediate to coupler from 0.95 to 1.05, although the relative quantities may vary depending upon the formulation and the desired colour, intensity or effect.

Couplers are generally meta-derivatives such as phenol, resorcinol and naphthol derivatives, m-aminophenols and m-phenylenediamines; which may be unsubstituted, or substituted on the amino group or benzene ring with alkyl, hydroxyalkyl or alkylamino groups.

Suitable couplers for use in part (i) include:

phenol, resorcinol and naphthol derivatives such as: naphthalene-1,7-diol; benzene-1,3-diol (commonly known as resorcinol); 4-chlorobenzene-1,3-diol (commonly known as 4-chlororesorcinol); naphthalen-1-ol (commonly known as 1-naphthol); 2-methyl-naphthalen-1-ol; naphthalene-1,5-diol; naphthalene-2,7-diol, benzene-1,4-diol; 2-methyl-benzene-1,3-diol (commonly known as 2-methylresorcinol); 7-amino-4-hydroxy-naphthalene-2-sulfonic acid; 2-isopropyl-5-methylphenol; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-dichloro-2-methylbenzene-1,3-diol; 4,6-dichlorobenzene-1,3-diol; 2,3-dihydroxy-[1,4]-naphthoquinone; 1-acetoxy-2-methylnaphthalene; and cosmetically acceptable salts thereof and combinations thereof.

m-phenylenediamines such as: m-phenylenediamine; 2,4-diaminophenoxyethanol; 2,6-diaminotoluene; N,N-bis(hydroxyethyl)-2,4-diaminophenetole; bis(2,4-diaminophenoxy)-1,3-propane; hydroxyethyl-2,4-diaminobenzene: 2-amino-4-(2-hydroxyethyl)amino anisole; aminoethyloxy-2,4-diaminobenzene; 2,4-diaminophenoxyacetic acid; 4,6-bis(hydroxyethyloxy) m-phenylenediamine; 2,4-diamino-5-methylphenetole; 2,4-diamino-5-hydroxyethyloxytoluene; 2,4-dimethoxy-1,3-diaminobenzene; 2,6-bis(hydroxyethylamino) toluene; and cosmetically acceptable salts thereof and combinations thereof. Preferred m-phenylenediamines include: m-phenylenediamine; 2,4-diaminophenoxyethanol; bis(2,4-diaminophenoxy)-1,3-propane; hydroxyethyl-2,4-diaminobenzene; 2-amino-4-(2-hydroxyethyl)amino anisole; 4,6-bis(hydroxyethyloxy)m-phenylenediamine; 2,4-diamino-5-methylphenetole; 2,4-diamino-5-hydroxyethyloxytoluene; 2,4-dimethoxy-1,3-diaminobenzene; 2,6-bis(hydroxyethylamino) toluene; and cosmetically acceptable salts thereof and combinations thereof.

m-aminophenols such as: m-aminophenol; 2-hydroxy-4-carbamoylmethylamino toluene; m-carbamoylmethylamino phenol; 6-hydroxybenzomorpholine; 2-hydroxy-4-aminotoluene; 2-hydroxy-4-hydroxyethylaminotoluene (commonly known as 2-methyl-5-hydroxyethylaminophenol); 4,6-dichloro-m-aminophenol; 2-methyl-m-aminophenol; 2-chloro-6-methyl-m-aminophenol; 2-hydroxyethyloxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol; 5-amino-4-methoxy-2-methylphenol; and cosmetically acceptable salts thereof and combinations thereof. Preferred m-aminophenols include: m-aminophenol; 6-hydroxybenzomorpholine; 2-hydroxy-4-aminotoluene; 2-hydroxy-4-hydroxyethylaminotoluene (commonly known as 2-methyl-5-hydroxyethylaminophenol); 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol; 5-amino-4-methoxy-2-methylphenol; and cosmetically acceptable salts thereof and combinations thereof.

heterocyclics such as: 1-phenyl-3-methyl-5-pyrazolone (commonly known as phenylmethylpyrazolone); 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(2-hydroxyethoxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol; 4-hydroxy-2,5,6-triaminopyrimidine; and cosmetically acceptable salts thereof and combinations thereof.

Particularly preferred couplers include: resorcinol; 4-chlororesorcinol; m-aminophenol; 1-naphthol; 4-amino-2-hydroxytoluene; 2-methyl-5-hydroxyethylaminophenol; 2,4-diaminophenoxyethanol; 2-methylresorcinol; bis(2,4-diaminophenoxy)-1,3-propane; 2-amino-4-hydroxyethylaminoanisole; 2-amino-3-hydroxypyridine; 1-acetoxy-2-methylnaphthalene; and cosmetically acceptable salts thereof and combinations thereof.

Combinations of any of the above described materials may also be used.

Specific examples of suitable primary intermediate and coupler combinations for use in the invention include:

resorcinol, m-aminophenol, 2-amino-4-hydroxyethyl anisole sulfate, 2,4-diaminophenoxyethanol 2HCl, 1-hydroxyethyl-4,5-diaminopyrazole sulfate and toluene-2,5-diamine sulfate;

p-phenylenediamine, m-aminophenol, N,N-bis(2-hydroxyethyl)-p-phenylenediamine sulfate and resorcinol;

p-phenylenediamine, N,N-bis(2-hydroxyethyl)-p-phenylenediamine sulfate, m-aminophenol, resorcinol, 1-naphthol and phenylmethylpyrazolone.

The total quantity of oxidative dye (i.e. primary intermediate(s) and optionally coupler(s)) in part (i) generally ranges from about 0.01 to about 15% by weight based on the total weight of part (i).

Darker shades are generally obtained by using higher concentrations of oxidative dyes, such as from about 3 to about 15% by weight based on the total weight of part (i).

Part (i) may also comprise one or more compatible direct dyes, in an amount sufficient to provide colouring, particularly with regard to intensity. Typically, such an amount will range from about 0.05 to about 4% by weight based on the total weight of part (i). Suitable direct dyes include: HC Red No. 13 (Hydrochloride); HC Yellow No. 4; HC Yellow No. 2; HC Red No. 3; 3-nitro-p-hydroxyethylaminophenol; 2-amino-6-chloro-4-nitrophenol; Acid Red 92; Disperse Black 9; HC Yellow No. 15; 4-nitro-o-phenylenediamine; Disperse Violet No. 1; HC Blue No. 2; Disperse Blue 3; Disperse Blue 377; Basic Red 51; Basic Orange 31; Basic Yellow 87; and mixtures thereof.

Part (i) comprises less than 1% oleic acid (also termed cis-9-octadecenoic acid or C18:1) by weight based on the total weight of part (i).

Preferably part (i) is substantially free of oleic acid. The term "substantially free" in this context means that oleic acid is not intentionally added to the composition, although incidental trace quantities may occur, such as no more than 0.1%, preferably no more than 0.01%, and more preferably from 0 to 0.001% by weight based on the total weight of part (i).

Part (i) will usually be formulated into a cosmetic preparation such as a cream, lotion, gel or emulsion, and so will generally contain other components commonly associated with the formulation of such products.

Preferably, part (i) comprises a phosphate ester compound. Suitable phosphate ester compounds in this context may be selected from:

i) mono-ester phosphates of alkoxylated fatty alcohols containing from about 12 to about 22 carbon atoms and alkoxylated with from about 1 to about 50 moles of an alkylene oxide (per mole of alkoxylated fatty alcohol), the alkylene oxide being selected from ethylene oxide, propylene oxide and mixtures thereof, i) di-ester phosphates of non-alkoxylated fatty alcohols containing from about 12 to about 22 carbon atoms, and mixtures thereof.

Preferably, the phosphate ester compound is a mixture of mono-ester phosphates of alkoxylated fatty alcohols (i) and di-ester phosphates of non-alkoxylated fatty alcohols (ii) more preferably the ratio of (i) to (ii) in such a mixture ranges from 1:10 to 10:1, more preferably from 1:9 to 3:1.

Phosphate ester compounds (i) and/or (ii) as described above can be formed by reacting alkoxylated and non-alkoxylated fatty alcohols, respectively, with phosphorus pentoxide ($P_2O_5$). This esterification process is well known in the art and will usually result in a blend of mono- and di-phosphate esters.

The alkoxylated fatty alcohols used in the esterification process preferably have the formula:

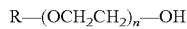

R—(OCH$_2$CH$_2$)$_n$—OH in which R is a branched or unbranched alkyl or alkenyl group having from about 12 to about 22 carbon atoms, more preferably from about 14 to about 20 carbon atoms, most preferably from about 16 to about 18 carbon atoms; and n has a value of from about 2 to about 20.

The non-alkoxylated fatty alcohols used preferably have the formula R—OH in which R is as defined above.

A preferred phosphate ester compound for use in the invention is a mixture of dicetyl phosphate and ceteth-10 phosphate.

The total quantity of phosphate ester compound in part (i) generally ranges from about 0.1 to about 10%, preferably from about 0.2 to about 5%, more preferably from about 0.3 to about 3.5% by weight based on the total weight of part (i).

Preferably part (i) comprises one or more fatty ($C_{10}$ to $C_{24}$) alcohols. Preferred fatty alcohols for inclusion in part (i) have the formula $R^1$—OH, in which $R^1$ is selected from branched or unbranched alkyl or alkenyl groups having from about 12 to 18 carbon atoms. Examples of such materials include lauryl alcohol, cetyl alcohol, stearyl alcohol and mixtures thereof.

The total quantity of fatty ($C_{10}$ to $C_{24}$) alcohols in part (i) generally ranges from about 2 to about 25%, preferably from about 3 to about 20%, more preferably from about 5 to about 15% by weight based on the total weight of part (i).

Most preferably part (i) comprises from 5 to 15% fatty ($C_{10}$ to $C_{24}$) alcohols selected from lauryl alcohol, cetyl alcohol, stearyl alcohol and mixtures thereof, by weight based on the total weight of part (i).

Other conventionally used adjuvants which may be usefully incorporated into part (i) for enhancing performance and/or consumer acceptability include:

organic solvents to assist in dissolving the primary intermediates and couplers (e.g. alcohols containing up to three carbon atoms such as ethanol and isopropanol, polyhydroxy alcohols such as propylene or hexylene glycol and their lower($C_1$ to $C_4$) alkyl ethers, such as ethoxy ethers);

surfactants to help dissolve the primary intermediates and couplers (e.g anionic or nonionic surfactants, such as sulfates of fatty alcohols, alkanolamides of fatty alcohols, alkyl sulfonates, alkylbenzene sulfonates, oxyethylated fatty alcohols, oxyethylated nonylphenols and mixtures thereof);

antioxidants to inhibit premature oxidation of oxidative colorant by air (e.g. ascorbic acid, erythorbic acid, or sodium sulfite);

fragrances or perfume oils; chelating agents; opacifying agents; buffers; dispersing agents; sequestering agents; humectants; and antimicrobials.

One or a mixture of any of the above adjuvants may be incorporated in part (i), in concentrations suitably ranging from about 0.001 to about 7.5%, by weight of the individual adjuvant based on the total weight of part (i).

The pH of part (i) is typically alkaline, and generally the pH is from 8 to 12, preferably 9 to 11. Any of a wide variety of alkaline reagents can be used to adjust the pH of part (i). Such alkaline reagents include ammonium hydroxide, sodium, potassium or calcium hydroxide, sodium or potassium carbonate, sodium phosphate, sodium silicate, guanidine hydroxide, or any one of the alkylamines or alkanolamines, for example, ethylamine, triethylamine, trihydroxymethylamine, ethanolamine, diethanolamine, aminomethyl propanol, aminomethyl propanediol and the like.

The aqueous colour developer part (ii) comprises an oxidizing agent in an amount sufficient to cause formation of dye chromophores from the primary intermediates and couplers. Typically, such an amount ranges from about 1 to about 20%, preferably from about 3 to about 15%, more preferably from about 6 to about 12%, by weight based on the total weight of part (ii). Suitable oxidizing agents in this context are peroxygen materials capable of yielding hydrogen peroxide in an aqueous medium such as: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal, preferably sodium, salts of perborates, percarbonates, perphosphates, persilicates, and persulphates, which may be incorporated as monohydrates, tetrahydrates or the like); alkali metal bromates; enzymes; and mixtures thereof. Preferred is hydrogen peroxide.

The pH of part (ii) is typically acidic, and generally the pH is from 2.5 to 6.5, preferably from 3 to 5. The pH of part (ii) may be adjusted using a pH modifier.

Preferably part (ii) comprises one or more fatty ($C_{10}$ to $C_{24}$) alcohols, which may be the same or different to the fatty alcohol(s) in part (i). Preferred fatty alcohols for inclusion in part (ii) have the formula $R^2$—OH, in which $R^2$ is selected from branched or unbranched alkyl or alkenyl groups having from about 16 to 18 carbon atoms. Examples of such materials include cetyl alcohol, stearyl alcohol and mixtures thereof.

The total quantity of fatty ($C_{10}$ to $C_{24}$) alcohols in part (ii) generally ranges from about 0.5 to about 10%, preferably from about 1 to about 7%, more preferably from about 3 to about 5% by weight based on the total weight of part (ii).

Most preferably part (ii) comprises from 3 to 5% fatty ($C_{10}$ to $C_{24}$) alcohols selected from cetyl alcohol, stearyl alcohol and mixtures thereof, by weight based on the total weight of part (ii).

Part (ii) comprises at least 5% stearic acid by weight based on total weight of part (ii). Stearic acid (also termed n-octadecanoic acid, or C18:0) is usually obtained from natural animal or vegetable oils and fats such as cottonseed oil, coconut fat, cocoa butter, palm kernel oil, corn oil, castor oil, rapeseed oil, soybean oil, sunflower oil, beef tallow, lard and mixtures thereof.

Commercial grades of stearic acid generally contain from about 39 to 95% by weight stearic acid, in admixture with varying relative concentrations of other fatty acids depending on the sources and processing methods used.

A preferred source of stearic acid for use in the invention is a mixture comprising about 40 to 50% by weight palmitic acid, about 50 to 55% by weight stearic acid and about 1 to 3% by weight myristic acid (by weight based on the total weight of the mixture). A commercially available example is VSTEARN™ SA11 Stearic Acid (ex Vantage Oleochemicals).

The content of stearic acid (C18:0) per se in part (ii) preferably ranges from 5 to 15%, and is optimally around 8 to 12% by weight based on the total weight of part (ii).

Part (ii) comprises less than 1% oleic acid (also termed cis-9-octadecenoic acid or C18:1) by weight based on the total weight of part (ii).

Preferably part (ii) is substantially free of oleic acid. The term "substantially free" in this context means that oleic acid is not intentionally added to the composition, although incidental trace quantities may occur, such as no more than 0.1%, preferably no more than 0.01%, and more preferably from 0 to 0.001% by weight based on the total weight of part (ii).

Part (ii) may also contain, to the extent compatible, various ingredients useful for enhancing performance and/or consumer acceptability, such as peroxide stabilizers, foam formers, etc.; and may incorporate one or more of the adjuvants referred to above.

A preferred ingredient for inclusion in part (ii) is a conditioning polymer containing cationic monomer units. Suitable conditioning polymers in this context include synthetic copolymers containing cationic monomer units. The cationic monomers for use in these copolymers can include dialkylaminoalkyl(meth)acrylamides, trialkylaminoalkyl (meth)acrylamides, dialkylaminoalkyl(meth)acrylates, trialkylaminoalkyl(meth)acrylates, dialkyldiallyl ammonium halides and the like. Examples of suitable conditioning polymers containing cationic monomer units for use in the invention include copolymers of acrylic acid or methacrylic acid with di ($C_1$-$C_4$ alkyl) diallyl ammonium halides such as in particular dimethyldiallyl ammonium chloride (DMDAAC). The copolymers may also incorporate other polymerisable nonionic monomers such as acrylic acid esters (preferably $C_1$-$C_4$ esters such as methyl acrylate), acrylamide and the like. Preferred conditioning polymers containing cationic monomer units for use in the invention are copolymers of DMDAAC and acrylic acid. Particularly preferred are copolymers of DMDAAC and acrylic acid in which the DMDAAC: acrylic acid weight ratio ranges from about 95:5 to about 50:50, ideally from about 95:5 to 65:35, based on total polymer weight.

The conditioning polymers for use in the invention may have a weight average molecular weight (as determined by gel permeation chromatography) ranging from about 5,000 to about 6,000,000, with the preferred molecular weight ranging from about 100,000 to about 5,000,000.

The preferred viscosity for the conditioning polymers ranges from about 4,000 to about 10,000 cps, as determined using a Brookfield LVF No. 4 spindle at 60 rpm.

A commercially available example of a conditioning polymer for use in the invention is MERQUAT® 280 (ex Lubrizol Corporation). MERQUAT® 280 contains 80:20 (w/w) DMDAAC:acrylic acid and has a molecular weight of approximately 1,000,000.

The total quantity of conditioning polymer in part (ii) suitably ranges from 0 to about 5%, preferably from about 0.1 to about 1%, more preferably from about 0.2 to about 0.5% by weight based on the total weight of part (ii).

Most preferably part (ii) comprises from 0.2 to 0.5% of a copolymer of DMDAAC and acrylic acid, by weight based on the total weight of part (ii)

Another preferred ingredient for inclusion in part (ii) is a hydrocarbon emollient. Particularly preferred are petroleum-derived hydrocarbon emollients, which may be characterised as purified hydrocarbons or mixtures of hydrocarbons obtained from petroleum and having chain lengths of from about $C_{10}$ to about $C_{100}$. Petroleum-derived hydrocarbon emollients within this chain length range include mineral oil and petrolatum. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of saturated hydrocarbons, in which the number of carbon atoms per hydrocarbon molecule generally ranges from about 10 to about 40. Petrolatum is the most preferred hydrocarbon emollient for inclusion in the second composition of the kit. Also known as petroleum jelly or mineral jelly, petrolatum may be generally characterised as a white to yellow homogeneous colloidal mixture of solid and high-boiling liquid hydrocarbons obtained from petroleum, with melting points typically ranging from about 35° to about 60° C. and molecular masses ranging from about 450 to about 1000. Its chief constituents are alicyclic hydrocarbons and straight or branched chain aliphatic hydrocarbons having from about 16 to about 40 carbon atoms.

The total quantity of hydrocarbon emollient in part (ii) suitably ranges from 0.1 to about 10%, preferably from about 0.5 to about 7%, more preferably from about 1 to about 4% by weight based on the total weight of part (ii).

Most preferably part (ii) comprises from 1 to 4% petrolatum, by weight based on the total weight of part (ii).

In order to colour the hair, part (i) and part (ii) are mixed together, usually shortly before use.

Preferably part (i) and part (ii) are mixed at a weight ratio ranging from 2:1 to 1:3, more preferably at a weight ratio ranging from 1:1 to 1:2.

Preferably part (ii) is packaged in a pot and part (i) is packaged in a pliable tube, so that the contents of the tube may be extruded into the pot by the consumer and part (i) and part (ii) mixed together in the pot before application to the hair.

On the hair, the mixture of part (i) and part (ii) forms a stable formulation, preferably with enough consistency and body to remain on the hair without significant dripping or running during the colouring period. The oxidative dye precursors diffuse into the hair together with the oxidizing agent from the colour developer. The dyes form within the hair fibre. Being large molecules, they remain in the hair and do not readily wash out with ordinary shampoos.

At the end of the colouring period, (generally about 5 to 45 minutes and preferably about 10 to 30 minutes), the formulation is washed from the hair with a plain water rinse. If necessary, the hair is washed with a shampoo and rinsed, for example with water or a weakly acidic solution, such as a citric acid or tartaric acid solution, and dried. Optionally, a separate conditioning product may also be applied.

The invention will be further illustrated by the following, non-limiting Examples, in which all percentages quoted are by weight based on total weight unless otherwise stated. Comparative examples (not according to the invention) are designated by a letter and Examples according to the invention are designated by a number.

EXAMPLES

A series of two-part oxidative hair colorant formulations were prepared having ingredients as shown in Table 1 below.

TABLE 1

|  | Control | Example A | Example 1 |
| --- | --- | --- | --- |
| Part (i) Colorant |  |  |  |
| cetearyl alcohol | 6.2 | 6.2 | 6.2 |
| dicetyl phosphate | 0.9 | 0.9 | 0.9 |
| ceteth-10 phosphate | 0.9 | 0.9 | 0.9 |
| propylene glycol | 6 | 6 | 6 |
| oxidative dye precursors | 6.4 | 6.4 | 6.4 |
| ammonia | 0.9 | 0.9 | 0.9 |
| ethanolamine | 3.2 | 3.2 | 3.2 |
| lauryl alcohol | 1.4 | 1.4 | 1.4 |
| myristyl alcohol | 0.6 | 0.6 | 0.6 |
| fragrance | 0.4 | 0.4 | 0.4 |
| sodium sulfite | 0.5 | 0.5 | 0.5 |
| sodium hydroxide | 0.2 | 0.2 | 0.2 |
| erythorbic acid | 0.4 | 0.4 | 0.4 |
| ceteareth-50 | 0.3 | 0.3 | 0.3 |
| EDTA | 0.2 | 0.2 | 0.2 |
| bisabolol | 0.1 | 0.1 | 0.1 |
| water | to 100 | to 100 | to 100 |
| Part (ii) Developer |  |  |  |
| hydrogen peroxide | 6 | 6 | 6 |
| cetearyl alcohol | 4 | 4 | 4 |
| ceteareth-20 | 1 | 1 | 1 |
| PEG-40 castor oil | 0.8 | 0.8 | 0.8 |
| petrolatum | 1 | 1 | 1 |
| Polyquaternium-22 | 0.09 | 0.09 | 0.09 |
| fragrance | 0.2 | 0.2 | 0.2 |
| phosphoric acid | 0.2 | 0.2 | 0.2 |
| sodium stannate | 0.1 | 0.1 | 0.1 |
| pentasodium pentetate | 0.03 | 0.03 | 0.03 |
| disodium pyrophosphate | 0.05 | 0.05 | 0.05 |
| oleic acid | — | 5 | — |
| stearic acid | — | 5 | 10 |
| water | to 100 | to 100 | to 100 |

The formulations were assessed for their colour delivery to hair, as follows:

For each test formulation, colorant part (i) and developer part (ii) were mixed in a weight ratio of 2:3 in a plastic mixing bowl using a brush for 1 minute.

Each test mixture was then applied to test hair switches 5 minutes, 30 minutes and 1 hour after mixing, using the following protocol:

Test hair switches (natural white European 2.5 g/6") were positioned on aluminium foil and a dose of 4 g of the mixture was applied per gram of hair. The paste was spread onto dry hair with a tinting brush, ensuring that each strand of hair was covered evenly by turning the switch and applying more product until all hair fibres were completely covered. The hair switch was wrapped in the aluminium foil, left for 35 minutes in a 30° C. oven, and rinsed completely for 1 min with flow-controlled tap water (35° C. and 4 L/min). The switches were then washed with an application of 0.1 g shampoo per gram of hair, followed by a 30 s agitation to create a lather. The hair was then rinsed under a running flow-controlled tap for 30 s. The washing process was then repeated to ensure removal of any product left at the surface of the hair, and the switches were then dried in a 50° C. oven for one hour.

The colour of the test switches after treatment as above was measured using a Konica Colorimeter.

The results are shown in Table 2 below:

TABLE 2

| | Colour delivery $\Delta E^*$ (s.d.) | | |
| --- | --- | --- | --- |
| Time after mixing | 5 min | 30 min | 1 h |
| Control | 0.00 (0.00) | 1.23 (0.40) | 0.65 (0.34) |
| Example A | 1.35 (0.24) | 3.93 (0.26) | 7.36 (0.76) |
| Example 1 | 1.00 (0.93) | 1.01 (0.40) | 1.42 (0.38) |

*The reference switch for $\Delta E$ is the control colorant applied after 5 minutes A series of two-part oxidative hair colorant formulations were prepared having ingredients as shown in Table 3 below.

TABLE 3

|  | Control | Example B | Example 2 |
| --- | --- | --- | --- |
| Part (i) Colorant |  |  |  |
| ammonia | 2.0 | 2.0 | 2.0 |
| cetearyl alcohol | 6.2 | 6.2 | 6.2 |
| dicetyl phosphate | 0.9 | 0.9 | 0.9 |
| ceteth-10 phosphate | 0.9 | 0.9 | 0.9 |
| propylene glycol | 6 | 6 | 6 |
| lauryl alcohol | 1.4 | 1.4 | 1.4 |
| myristyl alcohol | 0.6 | 0.6 | 0.6 |
| fragrance | 0.4 | 0.4 | 0.4 |
| erythorbic acid | 0.4 | 0.4 | 0.4 |
| sodium sulfite | 0.4 | 0.4 | 0.4 |
| ceteareth-50 | 0.3 | 0.3 | 0.3 |
| ethanolamine | 0.3 | 0.3 | 0.3 |
| EDTA | 0.2 | 0.2 | 0.2 |
| sodium hydroxide | 0.09 | 0.09 | 0.09 |
| bisabolol | 0.1 | 0.1 | 0.1 |
| oxidative dye precursors | 0.09 | 0.09 | 0.09 |
| water | to 100 | to 100 | to 100 |
| Part (ii) Developer |  |  |  |
| hydrogen peroxide | 12 | 12 | 12 |
| cetearyl alcohol | 4 | 4 | 4 |
| ceteareth-20 | 1 | 1 | 1 |
| PEG-40 castor oil | 0.8 | 0.8 | 0.8 |
| petrolatum | 1 | 1 | 1 |
| Polyquaternium-22 | 0.09 | 0.09 | 0.09 |
| fragrance | 0.2 | 0.2 | 0.2 |
| phosphoric acid | 0.2 | 0.2 | 0.2 |
| sodium stannate | 0.1 | 0.1 | 0.1 |
| pentasodium pentetate | 0.03 | 0.03 | 0.03 |
| disodium pyrophosphate | 0.05 | 0.05 | 0.05 |
| oleic acid | — | 5 | — |
| stearic acid | — | 5 | 10 |
| water | to 100 | to 100 | to 100 |

The formulations were assessed for their damage repair using the test protocol described above.

Test hair switches (dark brown European 2.5 g/6") were subjected to 5 cycles of treatment with each test formulation. After each treatment, damage repair is assessed using DSC (differential scanning calorimetry).

The results are shown in Table 4 below:

TABLE 4

| | Damage measurements (DSC) Denaturation temperature of proteins (s.d.) | | | |
|---|---|---|---|---|
| Time after mixing | 0 cycle | 1 cycle | 3 cycles | 5 cycles |
| Control | 146.93 (0.34) | 146.66 (0.30) | 142.30 (0.24) | 138.91 (0.57) |
| Example B | 146.93 (0.34) | 147.87 (0.15) | 146.34 (0.48) | 144.82 (0.26) |
| Example 2 | 146.93 (0.34) | 147.30 (0.44) | 146.02 (0.42) | 143.67 (0.44) |

CONCLUSIONS

The results show that the incorporation of stearic acid according to the invention provides damage repair (as evidenced by increased thermal stability of proteins to denaturation). It also has no impact on colour delivery (as evidenced by no significant difference in ΔE).

The oleic/stearic mixture of the comparative examples also shows some evidence of damage repair. However, it has a negative impact on colour delivery, with a difference of 7ΔE compared to the control when product is applied after 1 hour.

The invention claimed is:

1. A packaged composition for the oxidative coloration of hair which is formulated in two parts, the composition comprising:
   (i) an aqueous hair colorant part comprising one or more oxidative dye precursors, and less than 1% oleic acid by weight based on total weight of part (i);
   (ii) an aqueous colour developer part comprising one or more oxidising agents, at least 5% stearic acid by weight based on total weight of part (ii); and less than 1% oleic acid by weight based on total weight of part (ii);
   in which parts (i) and (ii) are adapted to be mixed together before application to the hair.

2. The composition according to claim 1, in which parts (i) and (ii) are both substantially free of oleic acid.

3. The composition according to claim 1, in which the pH of part (i) is from 9 to 11.

4. The composition according to claim 1, in which the pH of part (ii) is from 3 to 5.

5. The composition according to claim 1, in which the content of stearic acid in part (ii) ranges from 8 to 12% by weight based on the total weight of part (ii).

6. A method of colouring hair, comprising mixing parts (i) and (ii) of the composition according to claim 1, then applying the mixture to hair.

7. The method according to claim 6, wherein part (i) and part (ii) are mixed at a weight ratio ranging from 1:1 to 1:2.

* * * * *